United States Patent
Tinger et al.

(10) Patent No.: US 9,802,877 B2
(45) Date of Patent: Oct. 31, 2017

(54) PROCESS OF PRODUCING PARA-XYLENE BY ALKYLATION OF BENZENE AND/OR TOLUENE INCLUDING TREATMENT OF AN ALKYLATING AGENT TO REMOVE METAL SALTS

(71) Applicant: ExxonMobil Chemical Patents Inc., Baytown, TX (US)

(72) Inventors: Robert G. Tinger, Friendswood, TX (US); Indulis J. Eilands, League City, TX (US); John R. Porter, Friendswood, TX (US); Larry L. Iaccino, Seabrook, TX (US)

(73) Assignee: ExxonMobil Chemical Patents Inc., Baytown, TX (US)

(*) Notice: Subject to any disclaimer, the term of this patent is extended or adjusted under 35 U.S.C. 154(b) by 10 days.

(21) Appl. No.: 14/802,695

(22) Filed: Jul. 17, 2015

(65) Prior Publication Data
US 2016/0060188 A1    Mar. 3, 2016

Related U.S. Application Data

(60) Provisional application No. 62/043,785, filed on Aug. 29, 2014.

(51) Int. Cl.
*C07C 2/86* (2006.01)
*B01D 3/14* (2006.01)
*C07C 29/80* (2006.01)

(52) U.S. Cl.
CPC .............. *C07C 2/864* (2013.01); *C07C 29/80* (2013.01); *C07C 2529/06* (2013.01); *C07C 2529/40* (2013.01)

(58) Field of Classification Search
CPC ..................................................... B01D 3/141
See application file for complete search history.

(56) References Cited

U.S. PATENT DOCUMENTS

| 2,471,134 A | 5/1949 | Wright |
| 4,002,698 A | 1/1977 | Kaeding |

(Continued)

FOREIGN PATENT DOCUMENTS

| JP | 10-137598 | 5/1998 |
| WO | WO 2010/072836 | 7/2010 |
| WO | WO 2011/071977 | 6/2011 |

OTHER PUBLICATIONS

Abolpour et al. "Optimization of the reflux ratio for methanol-water stage distillation column", Res Chem Intermed, 2013, 39:681-692, published May 13, 2012.*

(Continued)

*Primary Examiner* — In Suk Bullock
*Assistant Examiner* — Ali Z Fadhel

(57) ABSTRACT

In a process and system for treatment of feed stocks comprising alkylating agent and metal salts, the metal salts are removed from the feedstock by an efficient combination of separations processes. The processes may take place in one or more stages, each stage taking place in one or more vessels. Such treatment processes may remove 99.9% or more of metal salts from a feedstock, while recovering 99.9% or more of the alkylating agent from the feedstock for use in an alkylation reaction, especially of aromatics such as toluene and benzene. Preferred alkylating agents include methanol and mixtures of carbon monoxide and hydrogen, for methylation of toluene and/or benzene. The methylation proceeds over an aluminosilicate catalyst and preferably yields para-xylene with 75% or greater selectivity.

13 Claims, 6 Drawing Sheets

(56) References Cited

U.S. PATENT DOCUMENTS

| | | | |
|---|---|---|---|
| 4,192,771 A | 3/1980 | Burbidge et al. | |
| 4,356,338 A | 10/1982 | Young | |
| 4,409,412 A | 10/1983 | Haag et al. | |
| 4,423,266 A | 12/1983 | Young | |
| 4,547,605 A | 10/1985 | Kresge et al. | |
| 5,227,558 A | 7/1993 | Shamshoum et al. | |
| 5,675,047 A | 10/1997 | Beck et al. | |
| 5,804,690 A | 9/1998 | Chang et al. | |
| 5,939,597 A | 8/1999 | Dessau et al. | |
| 6,028,238 A | 2/2000 | Beck et al. | |
| 6,046,372 A | 4/2000 | Brown et al. | |
| 6,048,816 A | 4/2000 | Brown et al. | |
| 6,156,949 A | 12/2000 | Brown et al. | |
| 6,423,879 B1 * | 7/2002 | Brown | B01J 29/40 502/245 |
| 6,504,072 B1 | 1/2003 | Brown et al. | |
| 6,506,954 B1 | 1/2003 | Brown et al. | |
| 6,538,167 B1 | 3/2003 | Brown et al. | |
| 6,617,482 B1 | 9/2003 | Venkat et al. | |
| 6,642,426 B1 | 11/2003 | Johnson et al. | |
| 6,846,966 B2 | 1/2005 | Lumgair, Jr. et al. | |
| 7,048,833 B2 | 5/2006 | Lumgair, Jr. et al. | |
| 7,074,979 B2 | 7/2006 | Van Egmond et al. | |
| 7,214,843 B2 | 5/2007 | Beech, Jr. et al. | |
| 7,238,846 B2 | 7/2007 | Janssen et al. | |
| 7,247,764 B2 | 7/2007 | Janssen et al. | |
| 7,249,469 B2 | 7/2007 | Porter | |
| 7,323,147 B2 | 1/2008 | Lumgair, Jr. et al. | |
| 7,385,100 B2 | 6/2008 | Beech, Jr. et al. | |
| 7,402,718 B2 | 7/2008 | Janssen et al. | |
| 7,453,019 B2 | 11/2008 | Janssen et al. | |
| 7,902,100 B2 | 3/2011 | Pujado | |
| 8,558,046 B2 | 10/2013 | Galloway, Jr. et al. | |
| 2002/0132731 A1 | 9/2002 | Loescher et al. | |
| 2004/0249226 A1 | 12/2004 | Wu et al. | |
| 2005/0006283 A1 | 1/2005 | Leung et al. | |
| 2006/0040821 A1 | 2/2006 | Pujado | |
| 2007/0142212 A1 | 6/2007 | Pujado | |
| 2007/0207915 A1 | 9/2007 | Pujado | |
| 2007/0243996 A1 | 10/2007 | Pujado | |
| 2011/0224469 A1 * | 9/2011 | Vincent | C07C 2/66 585/323 |

OTHER PUBLICATIONS

Gil et al. "Separation of ethanol and water by extractive distillation with salt and solvent as entrainer: process simulation", Brazilian Journal of Chemical Engineering, vol. 25, No. 01, pp. 207-215, Jan.-Mar. 2008.*

Pinho "Solubility of NaCl, NaBr, and KCl in Water, Methanol, Ethanol, and Their Mixed Solvents", J. Chem. Eng. Data, 2005, 50, 29-32.*

Zhao et al., "Sodium Deactivation of Fluid Catalytic Cracking Catalyst," in: "Deactivation and Testing of Hydrocarbon Processing Catalysts," Jun. 6, 1996, American Chemical Society, vol. 634, pp. 159-170.

* cited by examiner

PROCESS OF PRODUCING PARA-XYLENE BY ALKYLATION OF BENZENE AND/OR TOLUENE INCLUDING TREATMENT OF AN ALKYLATING AGENT TO REMOVE METAL SALTS

PRIORITY CLAIM

The present application claims priority to and the benefit of U.S. Provisional Application No. 62/043,785, filed Aug. 29, 2014, the disclosure of which is incorporated herein by reference in its entirety.

FIELD OF THE INVENTION

This invention relates to processes, systems, and apparatus for the production of an alkylating agent substantially free of metal salt. In addition, this invention relates to the production of alkylated aromatics, particularly para-xylene, using the purified alkylating agent.

BACKGROUND OF THE INVENTION

Alkylating agents, and particularly methylating agents, are an important feedstock in the production of alkyl aromatics such as xylenes by alkylation. Of the xylene isomers, para-xylene (often abbreviated PX) is of particular value for many reasons, including its use in the manufacture of terephthalic acid, which is an intermediate in the manufacture of synthetic fibers. Equilibrium mixtures of xylene isomers either alone or in further admixture with ethylbenzene generally contain only about 24 wt % para-xylene and separation of p-xylene from such mixtures has typically required absorption and/or multistage refrigeration steps. Such processes have involved high operation costs and resulted in only limited yields.

Recently, an improved process of toluene methylation by methylating agents has been developed using certain aluminosilicate zeolite molecular sieve catalysts that, when treated and used under appropriate conditions, may exhibit high selectivity to the para-xylene isomer in toluene methylation, with per-pass toluene conversion of at least about 15%. This important development has been described in numerous patents and publications, such as U.S. Pat. Nos. 4,002,698; 4,356,338; 4,423,266; 5,675,047; 5,804,690; 5,939,597; 6,028,238; 6,046,372; 6,048,816; 6,156,949; 6,423,879; 6,504,072; 6,506,954; 6,538,167; and 6,642,426, the entirety of each of which is incorporated herein by reference.

However, some molecular sieve catalysts that may be utilized in efficient aromatic alkylation, such as toluene methylation with high selectivity to para-xylene, may be sensitive to various contaminants that can "poison" the catalyst (i.e., reduce the activity of the catalyst and/or reduce its selectivity to a desired end product). Poisoning can shorten catalyst life, requiring more frequent regeneration and/or replacement, significantly adding to the costs of an aromatic alkylation process employing the catalyst.

SUMMARY OF THE INVENTION

Systems, apparatus, and methods are provided for treating a feedstock of alkylating agent to remove most or all metal salts therein. The treated feedstock may, thereafter, be used for producing alkylated aromatics and particularly para-xylene. More particularly, the feedstock is treated in one or more stages to remove most or all metal salts present therein before the feedstock is contacted with an aluminosilicate zeolite catalyst under conditions sufficient to produce an alkylated aromatic compound. Removing most or all metal salts from the alkylating agent prior to contacting the aluminosilicate zeolite catalyst reduces or prevents catalyst poisoning and thereby extends catalyst life.

Accordingly, one aspect of the present invention provides a process for treating a feedstock, in which a feedstock comprising alkylating agent and metal salt is separated in one or more stages to provide at least one alkylating agent-rich feed stream and a metal salt-rich discharge. The separation can take place in a single stage using a dividing-wall column. Alternatively or in addition, the separation can include multiple stages. The separation may include separating the feedstock into a first vaporized alkylating agent-rich feed stream and a metal salt-rich liquid blowdown. In some cases, the blowdown is further separated in one or more additional stages into at least an additional alkylating agent-rich vapor stream and a metal salt-rich liquid discharge. Alternatively, or in addition, the blowdown may be diverted for use in other processes not sensitive to metal salt content.

At least a portion of the alkylating agent-rich vapor feed stream(s) are reacted with one or more aromatic compounds in the presence of an aluminosilicate zeolite catalyst. Reaction of aromatic compounds and alkylating agent in the presence of the aluminosilicate zeolite catalyst yields alkylated aromatic products. In a preferred example, the aromatic compound is toluene and/or benzene and the alkylating agent is methanol and the reaction of in the presence of the aluminosilicate zeolite catalyst yields para-xylene.

In a further aspect, the present invention provides systems and apparatus for carrying out the various processes provided herein. Such systems and/or apparatus include a separation system for separating a feedstock comprising alkylating agent and metal salt into an alkylating agent-rich feed stream and a metal salt-rich discharge. The separation system may contain one or more vessels for separation in one or more stages. For example, a separations unit is provided comprising a dividing-wall column comprising at least a desalting zone and an alkylating agent recovery zone. Alternatively, multiple separations units may be provided, each separation unit being selected from among one or a combination of: a vapor/liquid separator such as a blowdown drum, a desalting unit, and a dividing wall column. A desalting unit may be a sorption separations unit such as an adsorption, absorption, and/or ion-exchange separations unit. The invention may additionally include an aromatic alkylation unit for alkylating one or more aromatic compounds with at least a portion of the alkylating agent-rich vapor feed stream provided by the separation system.

DETAILED DESCRIPTION OF THE EMBODIMENTS

Figure 1:
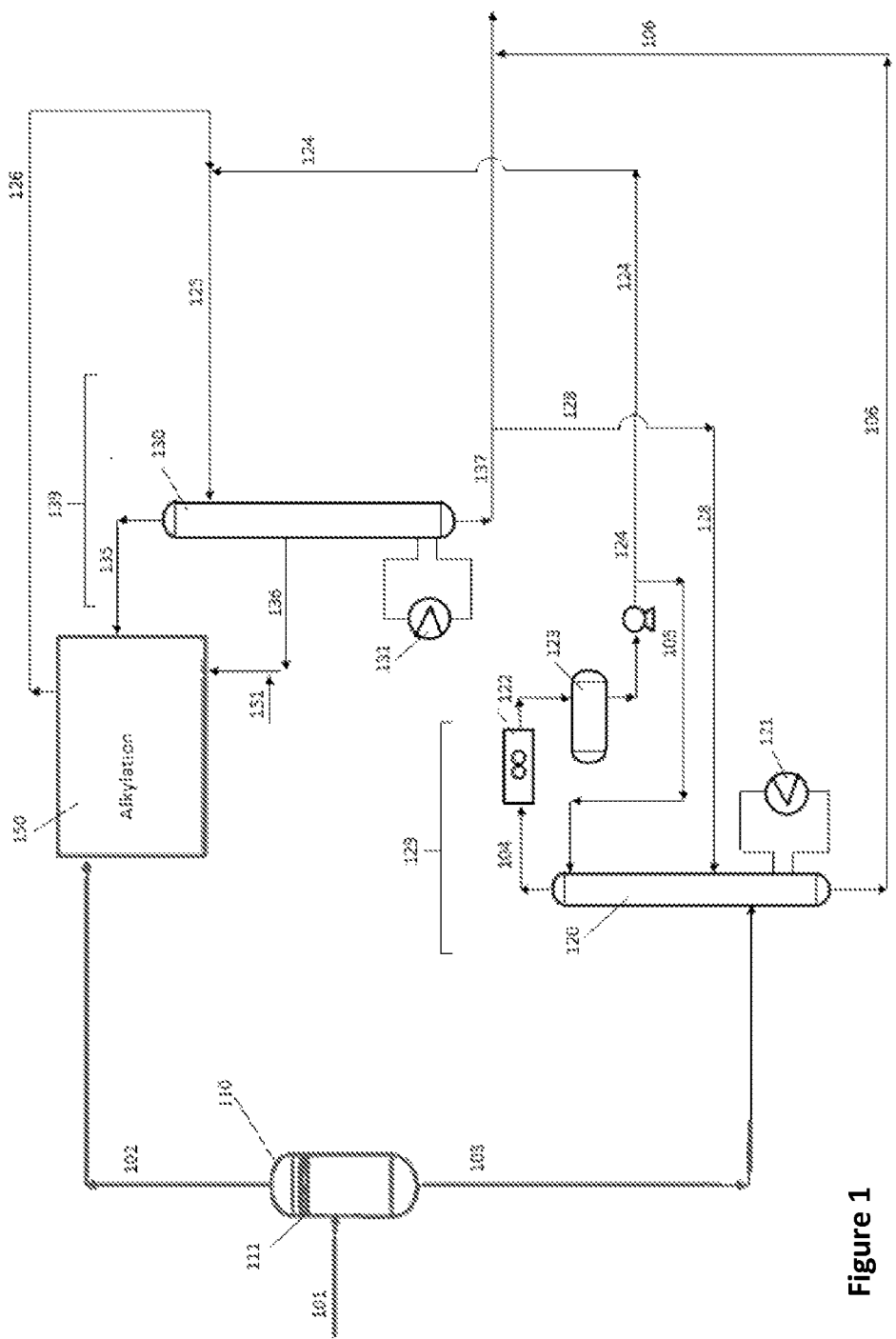
FIG. 1 is a flow diagram of a process for treating feedstock for the production of alkyl aromatics according to a first embodiment of the invention.

The present invention describes processes, systems, and apparatus for treating feedstock containing alkylating agent and metal salts, so as to remove most or all of the metal salts from the feedstock. The treated feedstock may be used for alkylating aromatics in the presence of an aluminosilicate zeolite catalyst, preferably methylation of benzene and/or toluene to form para-xylene. The treated feedstock advantageously may contain little or substantially no metal salt by the time it contacts the aluminosilicate zeolite catalyst, thereby reducing or avoiding catalyst poisoning by the metal salt and accordingly extending catalyst life.

A process according to some embodiments may include separating a feedstock comprising an alkylating agent and metal salt into at least an alkylating agent-rich feed stream and a metal salt-rich discharge. When a stream is described herein as being "rich," "rich in," or "enriched" in a specified species, it is meant that the wt % of the specified species in that stream is enriched relative to the feed stream prior to separation. When a stream is described as being "depleted" in a specified species, it is meant that the wt % of the specified species in that stream is reduced relative to the feed stream prior to separation. Thus, a post-separation stream is "alkylating agent-rich" when the wt % of alkylating agent in that stream is enriched relative to the wt % of alkylating agent in the corresponding stream prior to separation.

The alkylating agent-rich feed stream in some embodiments may further be reacted with one or more aromatic compounds in the presence of an aluminosilicate zeolite catalyst so as to carry out alkylation of at least some of the one or more aromatic compounds. In such embodiments, it is particularly important that the alkylating agent-rich feed stream have little to no metal salts so as to avoid or reduce poisoning of the aluminosilicate zeolite catalyst.

Aluminosilicate Zeolite Catalysts and Metal Salt Poisoning

Any method known in the art for adding alkyl groups to a phenyl ring can be used in the alkylation step of certain embodiments. In particular, the alkylation step may comprise methylation of a phenyl ring, such as methylation of benzene and/or toluene to form para-xylene. Thus, certain preferred embodiments include reaction (e.g., alkylation, and particularly methylation) in the presence of a highly para-selective aluminosilicate zeolite catalyst, such as that employed in U.S. Pat. Nos. 6,423,879 and 6,504,072, the entire contents of which are incorporated herein by reference. Such a catalyst comprises a molecular sieve having a Diffusion Parameter for 2,2-dimethylbutane of about 0.1-15 $sec^{-1}$, such as 0.5-10 $sec^{-1}$, when measured at a temperature of 120° C. and a 2,2-dimethylbutane pressure of 60 torr (8 kPa). As used herein, the Diffusion Parameter of a particular porous crystalline material is defined as $D/r^2 \times 10^6$, wherein D is the diffusion coefficient ($cm^2$/sec) and r is the crystal radius (cm). The required diffusion parameters can be derived from sorption measurements provided the assumption is made that the plane sheet model describes the diffusion process. Thus, for a given sorbate loading Q, the value $Q/Q_\infty$, where $Q_\infty$ is the equilibrium sorbate loading, is mathematically related to $(Dt/r^2)^{1/2}$ where t is the time (sec) required to reach the sorbate loading Q. Graphical solutions for the plane sheet model are given by J. Crank in "The Mathematics of Diffusion", Oxford University Press, Ely House, London, 1967, the entire contents of which are incorporated herein by reference.

A molecular sieve employed in a para-selective methylation process according to some embodiments is normally a medium-pore size aluminosilicate zeolite. Medium pore zeolites are generally defined as those having a pore size of about 5 to about 7 Angstroms, such that the zeolite freely sorbs molecules such as n-hexane, 3-methylpentane, benzene, and p-xylene. Another common definition for medium pore zeolites involves the Constraint Index test which is described in U.S. Pat. No. 4,016,218, which is incorporated herein by reference. In this case, medium pore zeolites have a Constraint Index of about 1-12, as measured on the zeolite alone without the introduction of oxide modifiers and prior to any steaming to adjust the diffusivity of the catalyst. Particular examples of suitable medium pore zeolites include ZSM-5, ZSM-11, ZSM-12, ZSM-22, ZSM-23, ZSM-35, ZSM-48, and MCM-22, with ZSM-5 and ZSM-11 being particularly preferred.

The medium pore zeolites described above are particularly effective for methylation processes of certain embodiments since the size and shape of their pores favor the production of p-xylene over the other xylene isomers. Conventional forms of these zeolites have Diffusion Parameter values in excess of the 0.1-15 $sec^{-1}$ range referred to above. However, the required diffusivity for the catalyst can be achieved by severely steaming the catalyst so as to effect a controlled reduction in the micropore volume of the catalyst to not less than 50%, and preferably 50-90%, of that of the unsteamed catalyst. Reduction in micropore volume is derived by measuring the n-hexane adsorption capacity of the catalyst, before and after steaming, at 90° C. and 75 torr n-hexane pressure.

Steaming of the zeolite is effected at a temperature of at least about 950° C., preferably about 950° C. to about 1075° C., and most preferably about 1000° C. to about 1050° C. for about 10 minutes to about 10 hours, preferably from 30 minutes to 5 hours.

To effect the desired controlled reduction in diffusivity and micropore volume, it may be desirable to combine the zeolite, prior to steaming, with at least one oxide modifier, such as at least one oxide selected from elements of Groups 2 to 4 and 13 to 16 of the Periodic Table, as numbered according to IUPAC, "Nomenclature of Inorganic Chemistry," at 51 (2005). Most preferably, said at least one oxide modifier is selected from oxides of boron, magnesium, calcium, lanthanum, and most preferably phosphorus. In some cases, the zeolite may be combined with more than one oxide modifier, for example a combination of phosphorus with calcium and/or magnesium, since in this way it may be possible to reduce the steaming severity needed to achieve a target diffusivity value. In some embodiments, the total amount of oxide modifier present in the catalyst, as measured on an elemental basis, may be between about 0.05 and about 20 wt %, and preferably is between about 0.1 and about 10 wt %, based on the weight of the final catalyst.

Where the modifier includes phosphorus, incorporation of modifier into the catalyst is conveniently achieved by the methods described in U.S. Pat. Nos. 4,356,338, 5,110,776, 5,231,064 and 5,348,643, the entire disclosures of which are incorporated herein by reference. Treatment with phosphorus-containing compounds can readily be accomplished by contacting the zeolite, either alone or in combination with a binder or matrix material, with a solution of an appropriate phosphorus compound, followed by drying and calcining to convert the phosphorus to its oxide form. Contact with the phosphorus-containing compound is generally conducted at a temperature of about 25° C. and about 125° C. for a time between about 15 minutes and about 20 hours. The concentration of the phosphorus in the contact mixture may be between about 0.01 and about 30 wt %. Suitable phosphorus compounds include, but are not limited to, phosphonic, phosphinous, phosphorous and phosphoric acids, salts and esters of such acids, and phosphorous halides.

After contacting with the phosphorus-containing compound, the porous crystalline material may be dried and calcined to convert the phosphorus to an oxide form. Calcination can be carried out in an inert atmosphere or in the presence of oxygen, for example, in air at a temperature of about 150° C. to 750° C., preferably about 300° C. to 500° C., for at least 1 hour, preferably 3-5 hours. Similar techniques known in the art can be used to incorporate other modifying oxides into the catalyst employed in the alkylation process.

When treated with oxide modifier according to any of the various manners described herein, a portion of the aluminum of the aluminosilicate zeolite catalyst may leave the zeolite's crystal structure, leaving behind a crystalline defect and forming amorphous aluminum oxide (e.g., aluminum phosphate where the oxide modifier comprises phosphorus), either within the zeolite channels or external to the zeolite's channels. Unlike other phosphorous-containing molecular sieves such as ALPOs (aluminophosphate molecular sieves) and SAPOs (silicoaluminophosphate molecular sieves), treated aluminosilicate zeolites of such embodiments do not include phosphorus among their ordered crystalline structure even after such treatment.

In addition to the zeolite and modifying oxide, an aluminosilicate catalyst employed in an alkylation process such as methylation of aromatics may include one or more binder or matrix materials resistant to the temperatures and other conditions employed in the process. Such materials include active and inactive materials such as clays, silica and/or metal oxides, such as alumina. The latter may be either naturally occurring or in the form of gelatinous precipitates or gels including mixtures of silica and metal oxides. Use of a material which is active, tends to change the conversion and/or selectivity of the catalyst and hence is generally not preferred. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the porous crystalline material include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification.

In addition to the foregoing materials, the porous crystalline material can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

The relative proportions of porous crystalline material and inorganic oxide matrix vary widely, with the content of the former ranging from about 1 to about 90% by weight and more usually, particularly when the composite is prepared in the form of beads, in the range of about 2 to about 80 wt % of the composite. Preferably, the matrix material comprises silica or a kaolin clay.

The methylation catalyst used in various embodiments may optionally be precoked. The precoking step may be carried out by initially loading uncoked catalyst into the methylation reactor. Then, as the reaction proceeds, coke is deposited on the catalyst surface and thereafter may be controlled within a desired range, typically from about 1 to about 20 wt % and preferably from about 1 to about 5 wt %, by periodic regeneration through exposure to an oxygen-containing atmosphere at an elevated temperature.

Aluminosilicate zeolite catalysts of various types according to the above description may exhibit heightened sensitivity to poisoning due to the presence of metal salts such as sodium salts in any compound contacted with such catalysts. A "metal salt" as used herein includes any salt of a metal of Group 1 or Group 2 of the Periodic Table of the Elements, such as a sodium salt, and further includes any salt of a transition metal, such as a copper salt. Further, as used herein, discussion of concentration and/or other content of a "metal salt" is intended to include to both the salt compound (e.g., sodium chloride, NaCl) and dissociated corresponding metal ions (e.g., $Na^+$). For example, in some instances, metal salt and/or metal ions may contact the aluminosilicate zeolite and reduce the acidity of the catalyst. Catalysts according to certain embodiments may include relatively few alumina sites (i.e., they may have high silica-alumina molar ratios, such as 250 or more in some embodiments), which impart acidity to the catalyst. Thus, contamination of even a small number of these sites by metal salts may have a significant impact on the lifetime of the catalyst due to the already small number of acidity-imparting alumina sites. Moreover, metal salts present in a feedstock even in small quantities may lead to buildup of metal ions in the catalyst over time. For instance, a feed stream having 0.32 wppm metal salt may lead to metal concentration of 8400 wppm on the aluminosilicate zeolite catalyst after 1 year under standard operating conditions. As another example, 1 wppm of metal salt may lead to buildup of 1,250 wppm of metal in the catalyst after 1 year of operation at about 1.5 weight hourly space velocity (WHSV) on the basis of catalyst volume. After 5 years, the metal concentration on the catalyst would be about 2,000 wppm. Removal of most or substantially all metal salts from any stream contacting the catalyst according to some embodiments could improve catalyst life by as much as two, three, four, or five times. For instance, in some embodiments, aluminosilicate zeolite catalysts may be kept in continuous operation without replacement or regeneration for at least any one of 4, 5, 6, 7, 8, 9, or 10 years according to various embodiments.

Sources of Metal Salt Poisoning

In some circumstances, metal salts may be introduced to the aluminosilicate zeolite catalyst when such salts are present in a feed stream contacting the catalyst. For instance, alkylation of aromatics over aluminosilicate zeolite catalyst takes place according to some embodiments by reaction between an alkylating agent feed stream and an aromatic feed stream. Particular embodiments involve methylation of benzene and/or toluene to form xylene, preferably para-xylene. Thus, certain preferred embodiments include feed stream of a methylating agent such as methanol, dimethyl ether, and/or a mixture of carbon monoxide and hydrogen, and feed stream of benzene and/or toluene contacting the catalyst. It will be appreciated that feed streams according to various embodiments may also include other methylating and/or alkylating agents, depending upon the desired alkylation. For instance, alcohols such as ethanol and propanol, and halides such as methyl, ethyl, propyl, and $C_4$+ halides may be suitable alkylating agents according to some embodiments.

Although some feed streams may include metal salts as residual compounds due to the method of commercial manufacture of those feeds, in many instances, metal salts may result from transportation. Taking methanol feedstock for example, metal salts are generally not present in methanol as it is typically commercially produced. However, transport and particularly ocean transport of the methanol frequently results in introduction of at least trace amounts of metal salts. In fact, the International Methanol Producers and Consumers Association (IMPCA) provides a commercial specification for methanol that includes <0.32 ppm Na, as indicated by a Cl spec of <0.5 ppm (the source of Cl being seawater). Seawater may enter methanol storage vessels on ships due to minor leaks, or due to storage tank washing between voyages with brackish water, or the like. Other alkylating agent feed stocks may be subject to the same pitfalls at least via transportation, if not also or instead due to their manufacture.

Therefore, depending upon the source of an alkylating agent feedstock, it may be necessary to treat that feedstock so as to remove metal salts like sodium salts, in accordance with some embodiments of the present invention.

Treatment of Feedstock

Some embodiments of the present invention provide processes, methods, and/or apparatus tailored to treat alkylating agent feedstock to provide a treated feedstock having the extremely low concentration of metal salts necessary for contacting the treated feedstock with an aluminosilicate zeolite catalyst.

A process according to several embodiments includes separating a feedstock comprising an alkylating agent and a metal salt into at least an alkylating agent-rich feed stream and a metal salt-rich discharge. The process according to some embodiments may further include reacting at least a portion of the alkylating agent-rich feed stream with one or more aromatic compounds in the presence of an aluminosilicate zeolite catalyst.

Separating the feedstock may comprise any one or more of several separation steps, and each step may entail one or more stages in one or more separations vessels. According to some embodiments, separation may comprise a blowdown separation step, comprising separating the feedstock into (i) an alkylating agent-rich vapor feed stream and (ii) a metal salt-rich liquid blowdown. The blowdown separation step may take place in one or more separation stages, such as one or more heating stages. The vapor feed stream (i) may then be passed to alkylation reaction over the aluminosilicate zeolite catalyst, while the blowdown (ii) may according to some embodiments be subjected to further treatment. Further blowdown treatment according to such embodiments includes further separation to recover alkylating agent while rejecting metal salts. In certain embodiments, blowdown treatment includes a desalting step and an alkylating agent recovery step. The desalting step and alkylating agent recovery step may take place in separate vessels in series, or they may both take place in a single vessel (such as a dividing-wall column).

In certain embodiments, the first blowdown separation step may be omitted, and feedstock passed directly to desalting/alkylating agent recovery separations, particularly in embodiments in which both the desalting and recovery steps take place in a single vessel.

On the other hand, according to other embodiments, the blowdown may not be subjected to additional treatment, but instead may be diverted to another use that is not sensitive to metal salt content (such as fuel blending or the like), thereby avoiding undesirable waste of feedstock while maintaining integrity of the aromatic alkylation process.

Respective aspects of feedstock treatment according to these and other various embodiments are each discussed in greater detail below.

Blowdown Separation

Figure 2:
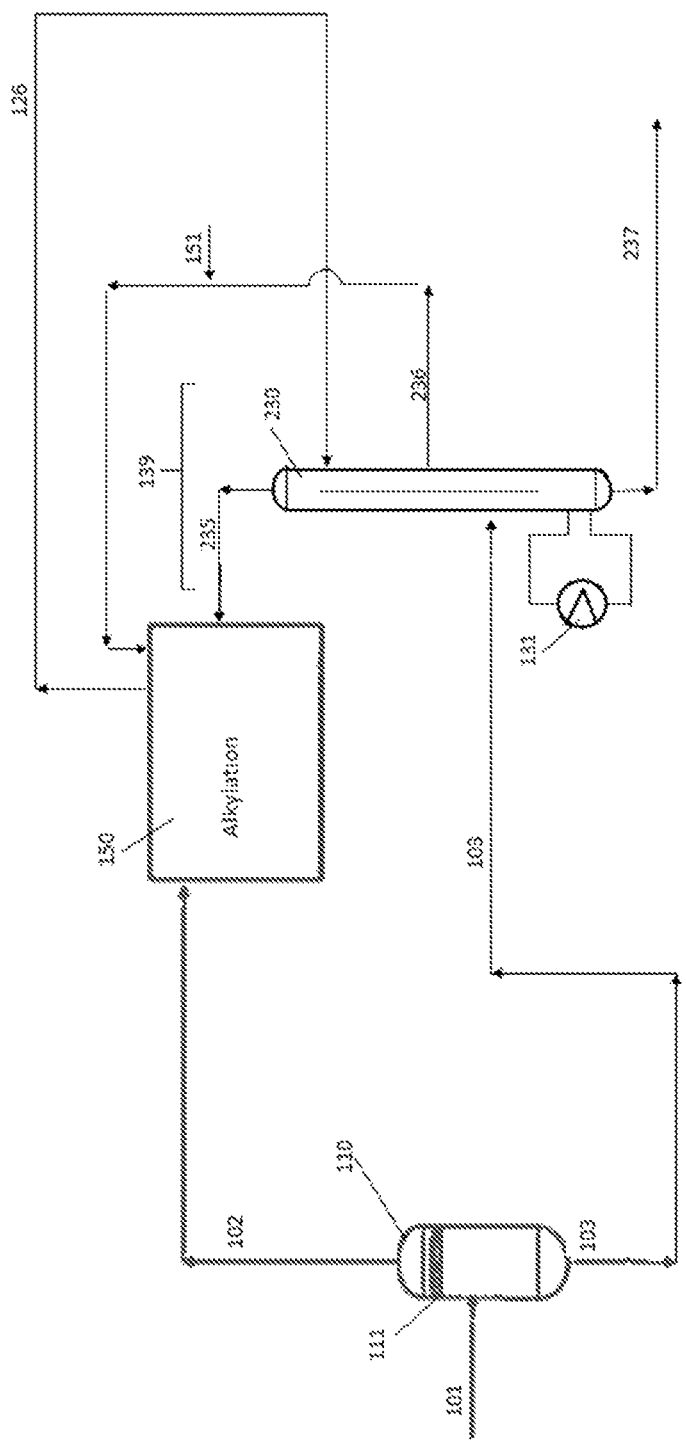
FIG. 2 is a flow diagram of a process for treating feedstock for the production of alkyl aromatics according to a second embodiment of the invention.

Treatment of feedstock comprising alkylating agent and metal salts (e.g., as entering via line 101 in FIG. 1) may be treated initially according to some embodiments by blowdown separation. As shown in FIGS. 1 and 2, this separation may be effected by a blowdown drum 110. The blowdown drum 110 may be or may comprise any suitable unit, such as a knockout drum, distillation column, thermosyphon, or any other suitable separation vessel(s) for separating the feedstock into an alkylating agent-rich feed stream and a metal salt-rich blowdown, as shown exiting the blowdown drum 110 in lines 102 and 103, respectively, in FIGS. 1 and 2. Preferably, the blowdown separation discharges vapor-phase alkylating agent-rich stream, and liquid phase metal salt-rich blowdown. In certain embodiments, as illustrated in FIGS. 1 and 2, the alkylating agent-rich feed stream may be delivered via line 102 directly to an aromatic alkylation reaction block 150 comprising an alkylation unit housing (or configured to house) the aluminosilicate zeolite catalyst. Optionally, this feed stream 102 may be heated by any suitable means between the blowdown separation and the aromatic alkylation reaction block. The blowdown may be taken via line 103 for further treatment, discussed in greater detail below.

The blowdown drum 110 or other separation unit may comprise a demister pad, such as the demister pad 111 shown in FIGS. 1 and 2. The demister pad may serve to reduce the amount of metal salt-containing liquid entrained in the alkylating agent-rich vapor stream, thereby further reducing the metal salt content of the vapor stream. A blowdown drum 110 or other separation unit may also include any number of heat exchangers and/or condensers as necessary to effectuate separation into the (preferably vapor phase) alkylating agent-rich feed stream and the (preferably liquid phase) metal salt-rich blowdown.

In some embodiments, a blowdown drum 110 or other unit effecting separation may be operated at conditions sufficient to create the alkylating agent-rich vapor stream and metal salt-rich blowdown, such that the alkylating agent-rich vapor stream comprises little or no metal salt. In some embodiments, the discharged alkylating agent-rich stream may comprise less than 0.1 wppm metal salts. In other embodiments, the alkylating agent-rich stream may comprise less than 0.09, 0.08, 0.07, 0.06, 0.05, 0.04, 0.03, 0.02, or 0.01 wppm metal salts. Operating conditions of the blowdown drum 110 or other blowdown separations unit in various embodiments will depend at least in part upon the alkylating agent present in the feedstock. For example, in various embodiments, operating conditions of the blowdown drum 110 may include: overhead pressure exiting the blowdown drum ranging from at least any one of 450, 500, 550, 575, 600, 625, and 650 kPa(g) (gauge) to at most any one of 700, 725, 750, 775, 800, 825, 850, 875, 900, 925, 950, 975, and 1000 kPa(g). Any integer value between the aforementioned end points may form an upper or lower operating endpoint, as well. For instance, in some embodiments, overhead pressure exiting the blowdown drum may range from about 579 to about 864 kPa(g). In other embodiments, the pressure may range from about 535 to about 915 kPa(g), and so on. Operating temperatures may range from at least any one of about 100, 105, 110, 115, 120, 125, 130, 135, and 140° C. to at most any one of about 120, 125, 130, 135, 140, 145, 150, 155, 160, 165, and 170° C. Any integer value between the aforementioned end points may form an upper or lower operating endpoint, as well. For example, operating temperature may range from about 123 to about 135° C., or in other embodiments, from about 111 to about 149° C., and so on.

Conveniently, operational parameters may instead or in addition be expressed in terms of the proportion of feedstock discharged as blowdown (that is, the percentage by weight of entering feedstock that is discharged in the blowdown). For instance, some embodiments include discharging blowdown comprising between about 3% to about 15% by weight of the feedstock. Other embodiments may include discharging blowdown comprising as little as 1, 2, 3, 4, 5, 6, 7, 8, 9, or 10% by weight of the feedstock, and comprising as much as 5, 6, 7, 8, 9, 10, 11, 12, 13, 14, 15, 16, 17, 18, 19, 20, 25, 30, 35, 40, 45, 50, or 55% by weight of the feedstock. For example, the blowdown in some embodiments may comprise between about 5% and about 10% by weight of the feedstock, or between about 6% and about 9%, or between about 7% and about 35%.

Figure 4:
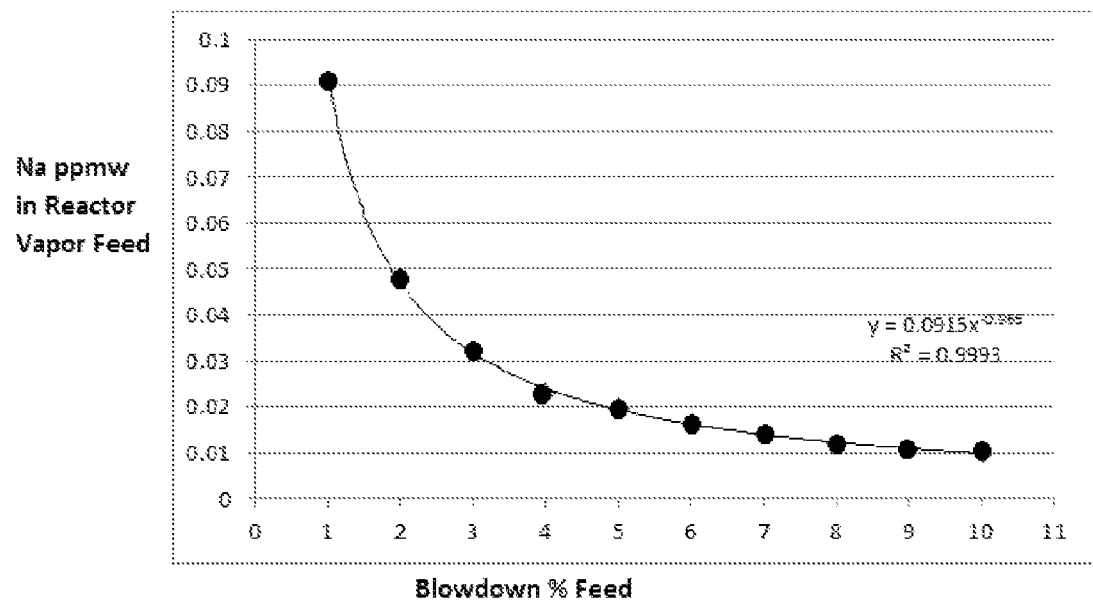
FIG. 4 is a graph illustrating operation of a process and system for treating feedstock according to various embodiments of the invention.

In operation according to certain embodiments, the blowdown proportion may bear a direct relationship to metal salt concentration remaining in the discharged alkylating agent-rich stream. FIG. 4 is a graph illustrating sodium concentration in a methanol stream fed to an aromatic alkylation reactor block after blowdown separation. The data is based upon calculations and mass balances on a blowdown separation of methanol feedstock having 1 ppmw sodium, wherein 0.1 wt % liquid is entrained in the vapor discharged by the blowdown drum, which is an amount of entrainment which may be encountered during typical operation of a blowdown drum with a demister tray. (In general, the finer the mesh on the demister tray, and/or the thicker the demister tray, and/or the greater the number of demister trays, the less liquid entrainment will be encountered.) As illustrated in FIG. 4, the direct relationship in these circumstances approximately follows the equation $y=0.0915x^{-0.965}$, where y is metal salt concentration in the discharged alkylating agent-rich feed stream (wppm) and x is blowdown as a percentage of the feedstock. In general, metal salt concentration in alkylating agent-rich streams discharged from blowdown separation according to some embodiments of the present invention may follow the relationship $y=\alpha x^{-0.965}$, where $\alpha$ is a constant directly proportional to the feedstock's initial metal salt concentration and the wt % of entrained liquid in the vapor.

As shown in FIG. 4, various embodiments of blowdown separation may therefore exhibit an asymptotic approach to just under 0.01 wppm metal salt concentration. Thus it can be seen that some preferred embodiments may involve discharge of blowdown comprising about 5% to about 9%, or about 6% to about 8%, or about 7%, by weight of the feedstock. For instance, as FIG. 4 illustrates, when operating at 7% blowdown, obtaining just a 0.005 wppm additional reduction in metal salt concentration requires an additional 3% of feedstock discharged to blowdown, i.e., operating so as to discharge 143% of the blowdown discharged by operating at 7% blowdown. This could result in a sizeable increase in operating expenses in further separations of the blowdown, and therefore may not be desired.

Further Treatment of Blowdown and/or Feedstock

Although inclusion of blowdown separation alone could in theory achieve the objective of passing feedstock to the aluminosilicate catalyst with little or no metal salt, it would do so at the cost of disposing a significant proportion of the alkylating agent in the feedstock (as much as 10% or more in some cases). This would likely result in unacceptable waste, including harmful environmental effects and poor process economics. According to some embodiments, the blowdown may be diverted to a process that is not sensitive to metal salt content, such as fuel blending. However, in some instances, it may be more desirable to retain as much of the alkylating agent as possible for the aromatic alkylation process. In such embodiments, additional stages of blowdown separation (e.g., additional heating separation stages similar to the first, such as additional blowdown drums in series) could resolve this problem. However, preferred embodiments include additional treatment processes that could yield enhanced efficiency over additional blowdown separation stages. In particular embodiments, the additional treatment recovers alkylating agent that is substantially free of all metal salts, to be added to the alkylating agent feed stream discharged from the blowdown drum. "Substantially free" may in some embodiments mean less than 1 wppb (0.001 wppm), or in other embodiments, less than 0.1, 0.01, or 0.001 ppb metal salts. Further, the more efficient the additional separation of the blowdown, the greater percentage blowdown from the blowdown drum the system can handle (therefore allowing the possibility of even lower salt concentrations with minimal added cost).

As noted previously, further treatment of blowdown may comprise additional separation processes. In some embodiments, further treatment may comprise any one or more of desalting and alkylating agent recovery, each of which may take place in any one or more separation stages (each stage taking place in one or more vessels). Any suitable separation process may be employed at each stage, including one or more of sorption (e.g., adsorption, absorption, ion exchange, cold clay treating, and the like), stripping, cascading, distillation, membrane separation, and the like.

Returning to the example embodiment of FIG. 1, blowdown may be separated in a two-stage process comprising: (1) desalting by separation into an alkylating agent-enriched liquid stream and a first metal salt-rich liquid effluent, followed by (2) alkylating agent recovery by separation of the alkylating agent-enriched liquid stream into an alkylating agent-enriched vapor stream and a second metal salt-rich liquid effluent. As shown in FIG. 1, the first separation stage (1) takes place in desalting section 129, and the second separation stage (2) takes place in alkylating agent recovery section 139. As noted, each separation stage may take place in one or more sub-stages according to various other embodiments not illustrated in FIG. 1. Specifically, according to FIG. 1, liquid blowdown is delivered via line 103 to the desalting section 129. The desalting section 129 may comprise a desalting column 120 of any suitable type (adsorption, cascade, absorption, distillation, fractionation, etc.). As shown in the embodiment of FIG. 1, desalting column 120 is a sorption column carrying out sorption (specifically absorption) of metal salts from the liquid blowdown using a water wash delivered via line 128. Any known unit for effecting a liquid-liquid or gas-liquid sorption (or other suitable separation process as noted previously) may be employed as a desalting column 120, such as liquid-liquid or vapor-liquid cascade configurations. Preferably, the desalting column 120 further comprises heating means 121 (e.g., a heat exchanger such as a reboiler) coupled to a bottom portion of the desalting column 120 to effect or aid in recovery of alkylating agent from the blowdown. In such configurations, the desalting column may discharge an alkylating agent-rich effluent (preferably liquid phase) in line 104, which optionally may be cooled (e.g., by condenser 122) and collection (e.g., in tank 123) before being pumped via lines 124 and 125 to alkylating agent recovery section 139. Optionally, a portion of the condensed effluent may additionally be recycled to a top portion of the desalting column 120, as shown by line 105 in FIG. 1. Any other separation unit and/or process suitable for separation into an overhead vapor phase and bottom liquid phase may be used, or alternatively, any separation unit and/or process suitable for separation into overhead alkylating agent-rich effluent and bottoms water-rich stream may be used as the desalting column (e.g., distillation and/or fractionation).

The desalting column 120 may operate under any suitable conditions to effect the above-described separation. In some instances, suitable conditions may depend at least in part upon the type of separation process employed in the desalting column 120. Preferably, both the alkylating agent-rich effluent and the metal salt-rich effluent leaving the column (e.g., via lines 104 and 106 in FIG. 1) are liquid phase, and accordingly, preferred operation of the desalting column 120 accordingly yields both streams in the liquid phase. Operating conditions of the desalting column may depend upon the alkylating agent present in the initial feedstock. For example, in embodiments in which the feedstock comprises methanol, the operating conditions of the desalting column 120 may include: exit overhead pressure ranging from at least any one of about 500, 525, 550, 575, 600, 625, 650, 675, 700, and 725 kPa(g) (gauge) to at most any one of about 750, 775, 800, 825, 850, 875, 900, 925, 950, 975, and 1000 kPa(g). Any integer value between the aforementioned end points may form an upper or lower operating endpoint, as well. For instance, in some embodiments, overhead pressure exiting the blowdown drum may range from about 623 to about 898 kPa(g). In other embodiments, the pressure may range from about 595 to about 944 kPa(g), and so on. Operating temperatures may range from at least any one of about 100, 105, 110, 115, 120, 125, 130, 135, and 140° C. to at most any one of about 115, 120, 125, 130, 135, 140, 145, 150, 155, 160, 165, and 170° C. Any integer value between the aforementioned end points may form an upper or lower operating endpoint, as well. For example, operating temperature may range from about 119° C. to about 130° C., or in other embodiments, from about 107 to about 149° C., and so on.

Moreover, in some embodiments, regardless of the identity of the alkylating agent, the alkylating agent-rich effluent may comprise about 70 to about 99% by weight of the liquid blowdown entering the desalting section 129. In various other embodiments, the alkylating agent-rich effluent may comprise at least about 70, 75, 80, 85, 90, 91, 92, 93, 94, 95, 96, 97, 98, or 99% by weight of the liquid blowdown, and at most about 80, 85, 90, 91, 92, 93, 94, 95, 96, 97, 98, 99, 99.5, or 99.9% by weight of the liquid blowdown. Further, the alkylating agent-rich effluent should comprise, in various embodiments, at least 95, 96, 97, 98, or 99% by weight of the alkylating agent entering the desalting column 120 in the liquid bottoms. In other embodiments, substantially all (e.g., 99.99, 99.999, 99.9999, 99.99999% or more, by weight) of the alkylating agent from the liquid bottoms exits the desalting column 120 in the alkylating agent-rich effluent via line 104.

In addition, the metal salt-rich liquid discharge (comprising at least metal salt and in applicable embodiments water, such as most or all of any water wash used in sorption or the like) leaving as the desalting column 120 bottoms in line 106 may in some embodiments comprise no more than 5, 4, 3, 2, 1, 0.5, 0.05, or 0.005% alkylating agent, by weight of the liquid discharge. Expressed in other terms, the liquid discharge should in various embodiments contain no more than 1%, preferably no more than 0.1, 0.01, 0.001, 0.0001, or 0.00001% by weight of the alkylating agent that entered the desalting column 120 in the liquid bottoms. That is, the far majority (and preferably substantially all) of the alkylating agent that enters the desalting column should be discharged in the overhead comprising the alkylating agent-rich effluent. Further, the metal-salt rich liquid discharged in line 106 in various embodiments comprises at least about 90, preferably more than 95, 96, 97, 98, 99, 99.9, or 99.99% by weight of the metal salts that were present in the inlet liquid blowdown in line 103.

As noted, the alkylating agent-rich effluent is discharged as overhead in line 104 and delivered to the alkylating agent recovery section 139 by line 125. The alkylating agent recovery section 139 as shown includes a stripper unit 130 for extracting an alkylating agent feed stream substantially free of metal salts. The alkylating agent feed stream may be provided to an alkylation reaction block 150, where alkylation such as methylation of toluene and/or benzene may take place in the presence of aluminosilicate zeolite catalyst. In preferred embodiments, the stripper unit 130 may also strip at least a portion of alkylating agent from a recovery stream recycled from the alkylation reaction block 150, as shown by recycle line 126 in FIG. 1. The stripper unit 130 may in some embodiments be a distillation column, fractionator, or any like separations unit suitable for extracting an alkylating agent feed stream from both the alkylating agent-rich effluent and the recovery stream. It may optionally include heating means 131 such as a heat exchanger and/or reboiler coupled to a bottom portion of the stripper unit 130.

In addition to the alkylating agent feed stream, the stripper unit 130 also ejects liquid discharge, preferably as the bottoms from the column, as shown in line 137 of FIG. 1. In certain preferred embodiments, at least a portion of the stripper unit bottoms in line 137 may be recycled to the desalting section 129 via line 128, where it may be employed in the separation process of that desalting section 129 (e.g., as the water wash in a sorption and/or cascade process).

Further, in certain embodiments, the stripper unit 130 furthermore ejects a sidestream in line 136 from a middle portion of the unit, the sidestream comprising steam and substantially no metal salts. The sidestream further may comprise substantially no alkylating agent (e.g., less than 100 ppm, less than 10 ppm, or less than 1 ppm, in various embodiments). The sidestream therefore may, in some embodiments, be added to a fresh aromatic feed 151 entering the alkylation reactor block 150. The addition of steam sidestream to the fresh aromatic feed raises the temperature to the high operating temperatures required for aromatic alkylation according to some embodiments (e.g., temperatures ranging from any one of about 400, 450, 475, 500, 525, and 550° C. up to any one of about 500, 525, 550, 575, 600, 625, 650, 675, and 700° C.). The addition of steam sidestream to fresh aromatic feed further reduces the partial pressure of the aromatic compounds fed to an aromatic alkylation reaction unit, which helps prevent coking. Because processes, systems, and apparatus of certain embodiments eliminate the presence of metal salts in this sidestream, the sidestream may provide the above benefits without the downside of metal salts contacting the aluminosilicate zeolite catalyst in an aromatic alkylation reaction unit.

The stripper unit 130 may operate under conditions sufficient to discharge at least the alkylating agent-rich vapor feed stream, the metal salt-rich liquid discharge, and the sidestream. In some embodiments, the alkylating agent-rich vapor feed stream comprises at least 20% by weight (of the vapor feed stream) alkylating agent. In some embodiments, the alkylating agent-rich vapor feed stream comprises at any one of 5, 10, 15, 20, 25, 27, 30, 35, and 40% by weight alkylating agent, and at most any one of 10, 15, 20, 25, 27, 30, 35, 40, 45, 50, 55, 60, 65, and 70% by weight alkylating agent. The balance may comprise mostly water (steam), with minor amounts (less than 5, 4, 3, 2, 1 or 0.5% by weight of total feed stream in various embodiments) of trace hydrocarbon impurities which may be present, e.g., due to an alkylating agent recovery recycle feed from a reaction block to the dividing-wall column 500. Further, the alkylating agent-rich feed stream discharged from the stripper section 139 should be substantially free of metal salts when carried out according to preferred embodiments. As noted, the alkylating agent-rich vapor feed stream further comprises water and/or steam. In certain embodiments, the alkylating agent-rich vapor feed stream comprises at least 50% by weight water and/or steam. The alkylating agent-rich vapor feed stream may comprise at least any one of about 30, 35, 40, 45, 50, 55, 60, 65, 70, 73, 75, 80, 85, or 90% by weight water (steam), and at most any one of about 60, 65, 70, 73, 75, 80, 85, 90, and 95% by weight water (steam). The presence of sufficient amounts of steam (such as the amounts disclosed herein) in the alkylating agent-rich vapor feed stream in an aromatic alkylation reaction using methylating agents as alkylating agents advantageously may improve selectivity to alkylated aromatics (such as xylenes, in particular para-xylene), as opposed to production of products which are undesired in certain embodiments, such as olefins. Advantageously, then, separations operations may at this point focus primarily on reducing entrained liquid (and thereby entrained metal salt) present in the overhead vapor stream in order to provide an alkylating agent-rich vapor feed stream comprising substantially no metal salts (i.e., less than 1, 0.1, or 0.01 ppm by weight in various embodiments).

The liquid discharge in the bottoms of stripper unit 130 preferably includes no more than 1, 0.1, 0.01, or 0.001 ppb by weight alkylating agent. Preferably, the liquid discharge contains substantially all (in various embodiments, at least 99.9, 99.99, 99.999, or 99.9999% by weight) of the metal salts in the alkylating agent-rich liquid effluent fed to the stripper unit 130 from the desalting column 120.

In summary, recall that (i) the metal salt-rich liquid effluent discharged via line 106 from the desalting column 120 comprises less than 1%, preferably no more than 0.1, 0.01, 0.001, 0.0001, or 0.00001% by weight of the alkylating agent that entered the desalting column 120 in the liquid bottoms; and further that (ii) the metal salt-rich liquid discharge purged from the stripper unit 130 via line 137 comprises less than 1, 0.1, 0.01, or 0.001 ppb by weight alkylating agent in various embodiments, it can be seen that the further treatment of the blowdown (e.g., in desalting section 129 and alkylating agent recovery section 139) results in loss of substantially none of the alkylating agent originally present in the liquid blowdown (i.e., less than 1, 0.1, or 0.01 ppm by weight in various embodiments). This indicates that substantially all of the alkylating agent present (e.g., all but 1 ppm, or 99.9999% or more) in the liquid blowdown is recovered in the further treatment according to certain embodiments, while being substantially free of metal salts. Thus, some embodiments provide for further treatment of blowdown resulting in recovery of a feed stream comprising substantially all alkylating agent in the liquid blowdown, while comprising substantially none of the metal salt from the liquid blowdown. According to such embodiments, then, the only source of metal salt fed to the aluminosilicate zeolite catalyst is in the first alkylating agent-rich stream discharged from the blowdown drum.

Dividing-wall Column

Figure 3:
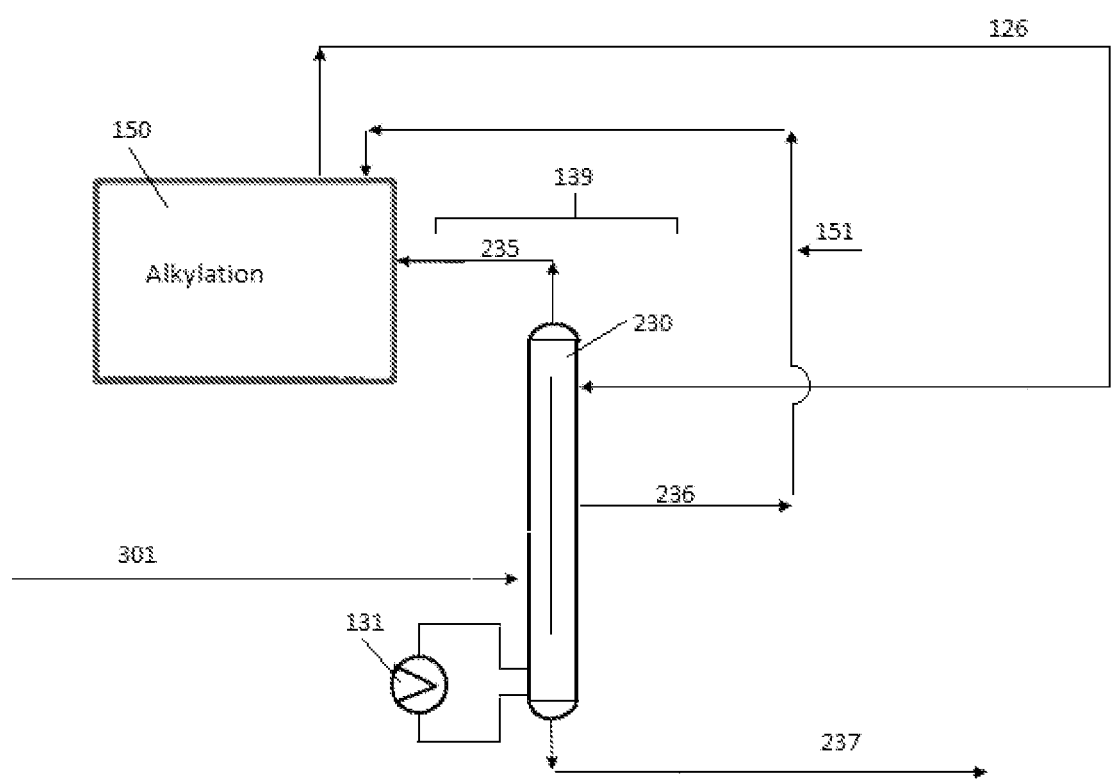
FIG. 3 is a flow diagram of a process for treating feedstock for the production of alkyl aromatics according to a modification of the second embodiment of the invention.

In certain embodiments, as noted previously, the further blowdown treatment (e.g., desalting and alkylating agent recovery, such as by sorption and stripping) may take place substantially in a single vessel, which may be a dividing-wall unit. Processes according to such embodiments may be carried out by a system configured as illustrated in FIG. 3, wherein the liquid blowdown is fed via line 103 to a single dividing-wall unit 230, which serves the combined functions of the desalting column 120 and the stripper unit 130 of FIG. 1. In particular, according to some embodiments, the dividing-wall unit 230 discharges at least an alkylating agent-rich feed stream (e.g., via line 235 in FIG. 2); a sidestream (line 236); and a metal salt-rich liquid discharge (line 237), corresponding to each stream respectively discharged from the stripper unit 130 in lines 135, 136, and 137 of embodiments according to the example of FIG. 1. The dividing-wall unit 230 may operate within any of the temperature and pressure conditions previously described with respect to the desalting column 120.

FIG. 3 illustrates a further embodiment utilizing a dividing-wall unit 230, wherein the initial blowdown separation of the feedstock may optionally be skipped. Thus, feedstock comprising alkylating agent and metal salt is fed directly via line 301 to the dividing-wall unit 230. In such embodiments, the dividing-wall unit operation may optionally involve additional trays (actual or theoretical), or operation at decreased temperature to ensure the absence or near-absence of metal salts in the overhead. In other embodiments, however, the dividing-wall unit 230 may be operated in substantially the same manner as in embodiments that include other separations such as initial blowdown.

Certain embodiments wherein feedstock is delivered directly to the dividing-wall unit 230 may take advantage of the need for steam in the alkylating agent-rich feed stream discharged in overhead line 235 according to some embodiments, as discussed previously. For instance, use of a dividing-wall unit may simplify the separation of metal salts from alkylating agent feeds by virtue of being able to operate at higher temperatures (e.g., to ensure presence of both steam and alkylating agent in the overhead), thus ensuring that no metal salts are present in the overhead feed stream in line 235, while also avoiding the need for further separations of steam from that overhead feed stream (as opposed to processes such as olefin-synthesis from alkylating agents, wherein operation at such conditions would necessitate separation of the steam in the feed stream, among other further modifications).

Figure 5:
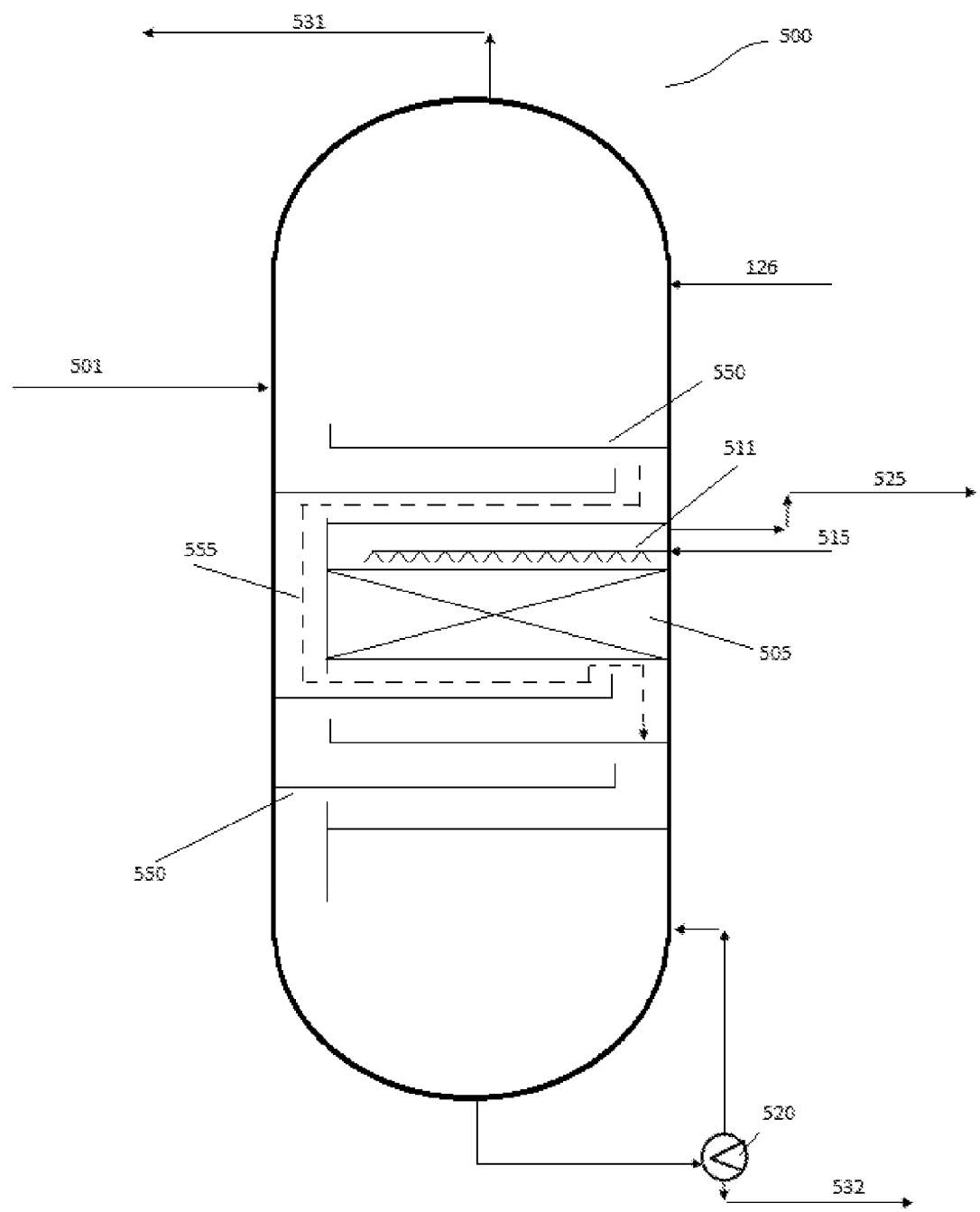
FIG. 5 is a schematic diagram illustrating an apparatus for treating feedstock for the production of alkyl aromatics according to a further embodiment of the invention.

FIG. 5 is a schematic illustrating an example dividing-wall unit according to some embodiments. The embodiment shown in FIG. 5 illustrates a dividing-wall column 500 comprising a desalting zone or portion 505 embedded among an alkylating agent recovery zone or portion 510, which in the embodiment of FIG. 4 comprises a plurality of trays 550 (in other embodiments, the alkylating agent recovery zone or portion 510 may comprise packing, a fixed, fluid, or fluidized fluid bed, or the like). The number of trays 550 shown in FIG. 5 is not necessarily representative; for instance, more trays 550 may be present above, below, or both above and below the desalting zone or portion 505. In particular, more trays 550 may be present above the desalting shown in embodiments wherein it is desired to eject a sidestream via line 525 comprising substantially no alkylating agent (discussed later).

The column 500 additionally includes heating means such as a reboiler 520 fluidically coupled to (i.e., in fluid communication with) a bottom portion of the column 500 so as to provide reflux of the bottoms discharged from the column via line 532. The column 500 is preferably operated at a temperature sufficient to create a vapor phase overhead of alkylating agent-rich feed stream, which may be discharged via line 531 to, e.g., an aromatic alkylation reaction block. As vapor phase comprising alkylating agent rises through the trays 550 of the alkylating agent recovery zone or portion 510, it passes through the embedded desalting zone or portion 505, which as shown in FIG. 5 may be a dis-entrainment zone, wherein water wash 511 is provided via line 515 to reduce entrainment of liquid phase within the vapor phase passing through the desalting zone. The reduction of entrainment may in some embodiments occur via a sorption process (e.g., liquid-gas absorption), or by any other suitable means of reducing entrained liquid in the vapor phase. The wash contacts at least a portion of the vapor phase and effects removal (e.g., adsorptive and/or absorptive removal, and/or condensation) of liquid (including metal salts dissolved therein) from the vapor phase as the vapor phase travels up the column 500, while liquid phase comprising metal salts falls to the bottom of the column to be discharged in the bottoms via line 532. The desalting zone or portion 505 of some embodiments may be arranged as shown in FIG. 5, such that liquid phase comprising metal salts in the alkylating agent recovery portion falls around, rather than through, the desalting zone or portion 505, as shown by liquid phase path 555 in FIG. 5. Further, the desalting zone or portion 505 may include packing, such as crinkly wire mesh screen (CWMS), trays, a fluid, fluidized, or fixed bed, or the like, to enhance the embedded separation taking place therein. For instance, where adsorptive separation takes place, the desalting zone or portion 505 may include a fluid, fluidized, or fixed bed.

The alkylating agent-rich feed stream, as noted, is discharged as vapor via line 531. In various embodiments, this feed stream may comprise at least any one of 5, 10, 15, 20, 25, 27, 30, 35, and 40% by weight alkylating agent, and at most any one of 10, 15, 20, 25, 27, 30, 35, 40, 45, 50, 55, 60, 65, and 70% by weight alkylating agent. The balance may comprise mostly water (steam), with minor amounts (less than 5, 4, 3, 2, 1 or 0.5% by weight of total feed stream in various embodiments) of trace hydrocarbon impurities which may be present, e.g., due to an alkylating agent recycle feed from a reaction block to the dividing-wall column 500 (delivering, among other things, unreacted alkylating agent from an aromatic alkylation, which stream may comprise trace hydrocarbon impurities).

The metal salt-rich bottoms (discharged via line 532) preferably contains less than 1% by weight alkylating agent and more than 99% by weight water (the water including metal salts). In certain embodiments, the bottoms comprise less than 1 ppb, 0.1 ppb, 0.01 ppb, or 0.001 ppb by weight alkylating agent. Preferably, the bottoms contains substantially all (in various embodiments, at least 99.9, 99.99, 99.999, or 99.9999% by weight) of the metal salts originally present in the blowdown or feedstock fed to the dividing-wall column via line 501.

In addition, a vapor phase sidestream is drawn off a middle portion of the column 500 via line 525, e.g. via one of the trays above the desalting zone 505. The sidestream comprises mostly water (steam), preferably at least 80, 90, 95, 98, 99, 99.5, 99.9, or 99.99% by weight water in various embodiments. The sidestream comprises substantially no metal salts, and may comprise at most 0.01, 0.1, 1, 2, 5, 10, or 20% alkylating agent in various embodiments. The sidestream may, like the sidestream of some previously described embodiments, be mixed with aromatic feed to an aromatic alkylation reaction block.

In summary, as with embodiments in which further treatment of blowdown is performed in a desalting step and then an alkylating agent recovery step, treatment by dividing-wall column (of either blowdown or feedstock) may result in recovery of substantially all of the alkylating agent in the blowdown or feedstock initially fed to the dividing wall column, with such recovered alkylating agent stream containing substantially no metal salts. Further, treatment processes employing a dividing-wall column comprising a desalting zone, as with embodiments just described, may provide the additional advantage of desalting any alkylating agent fed to the dividing-wall column in an alkylating agent recycle stream (e.g., recycled from an aromatic alkylation reaction block). This advantageously may remove at least some, if not all, metal salts that may be present in the recycle stream (due, e.g., to trace metal salts fed to the reactor by other means, or from an alkylating agent-rich vapor stream discharged from a blowdown separation, in embodiments where such separation is employed).

Thus, in accordance with the processes and systems of various embodiments just described, some embodiments of the present invention may provide a dividing-wall separations unit comprising: (i) an alkylating agent recovery zone or portion comprising a plurality of trays and (ii) a desalting zone or portion disposed among the alkylating agent recovery zone or portion. The alkylating agent recovery zone or portion of some embodiments may comprise a plurality of trays, such that the desalting zone or portion is disposed between at least two of the plurality of trays. According to certain embodiments, the alkylating agent recovery zone may be a stripping zone, which may be configured to effect stripping of an alkylating agent from a liquid in the alkylating agent recovery zone. In applicable embodiments, the trays may be disposed substantially horizontally within the dividing-wall unit and arranged in a vertical stack, with space between each tray, as in a distillation column. The desalting portion may be disposed between two of the trays. The two trays between which the desalting portion is disposed may in some embodiments be spaced farther apart than any other two trays in the alkylating agent recovery portion. In arrangements according to embodiments such as that shown in FIG. 5, the alkylating agent recovery portion of the dividing-wall separations unit may therefore in essence be split into two sub-portions by the desalting portion. As also shown in FIG. 5, the desalting portion may comprise a dis-entrainment zone, which may operate according to the above description of the embedded desalting zone or portion 505 (e.g., via sorption and/or condensation for removal of entrained liquid from the vapor phase). The dis-entrainment zone may comprise a demisting pad (e.g., to further aid in removal of liquids entrained in a vapor contacting the demisting pad).

The dividing-wall separations unit may further comprise any one or more of: (i) a feed inlet; (ii) a recycle inlet; (iii) an overhead outlet disposed at a top portion of the dividing-wall separations unit; (iv) a sidestream outlet; and (v) a bottoms outlet disposed at a bottom portion of the dividing-wall separations unit. The sidestream outlet may be disposed on the dividing-wall unit above the desalting portion and below the overhead outlet, as shown in FIG. 5. In embodiments wherein the desalting portion comprises a dis-entrainment zone, the dividing-wall separations unit may further comprise (vi) a wash inlet (exemplified by water-wash line 515 in FIG. 5). The (i) feed inlet may be configured to receive liquid alkylating agent feedstock and/or liquid blowdown; the (ii) recycle inlet may be in fluid communication with an aromatic alkylation reaction unit and configured to receive a stream comprising unreacted alkylating agent from the aromatic alkylation reaction unit; the (iii) overhead outlet may be configured to discharge an overhead stream comprising alkylating agent-rich feed stream and/or steam, and it may further be in fluid communication with the aromatic alkylation reaction unit (e.g., so as to deliver the alkylating agent-rich feed stream and/or steam to the reaction unit); the (iv) sidestream outlet may be configured to discharge steam, and in some embodiments, substantially no alkylating agent, and may further be combined with an aromatic feed stream and be in fluid communication with the aromatic alkylation reaction unit; the (v) bottoms outlet may be configured to discharge a liquid bottoms comprising substantially all metal salts present in the feed inlet stream; and the (vi) wash inlet may be configured to receive a wash such as a liquid sorbent to be dispersed (e.g., sprayed, cascaded, or otherwise discharged) into the desalting portion of the dividing-wall separations unit.

In other embodiments, the dividing-wall separations unit may be arranged such that the desalting portion is not embedded within the alkylating agent recovery portion. Instead, for instance, the desalting portion and alkylating agent recovery portion may be arranged beside each other in a dividing-wall column, with a vertical dividing wall separating the two (as stylized, e.g., by the simplified diagram of the dividing-wall column 230 of FIGS. 2 and 3). In such embodiments, each of the desalting portion and the alkylating agent recovery portion may operate substantially as the separate units would operate. That is, for example, the desalting portion may function as a desalting unit such as a desalting column, discussed previously, with the overhead alkylating agent-rich effluent delivered over the dividing wall to the alkylating agent recovery portion and the bottoms liquid discharge delivered to the bottom portion of the alkylating agent recovery portion through or around a bottom portion of the dividing wall. Further, in such embodiments, the alkylating agent recovery portion may operate substantially as a separate alkylating agent recovery unit (e.g., a stripper unit, fractionation or distillation unit, or the like, discussed previously).

Aromatic Alkylation

As noted throughout, various embodiments may further provide for reacting at least part of the alkylating agent-rich feed stream(s) produced by the various treatment methods and systems with one or more aromatic compounds in the presence of an aluminosilicate zeolite catalyst. Such reaction may take place in an aromatic alkylation reaction block. As also noted, aromatic alkylation can be carried out with any known alkylating agent, but preferred alkylation includes methylation of benzene and/or toluene, and preferred methylation agents include methanol, and/or a mixture of carbon monoxide and hydrogen, and/or dimethyl ether.

Suitable conditions for the methylation reaction include a temperature from 350 to 700° C., such as from 500 to 600° C., a pressure of from 100 and 7000 kPa absolute, a weight hourly space velocity of from 0.5 to 1000 $hr^{-1}$, and a molar ratio of toluene to methanol (in the reactor charge) of at least about 0.2, e.g., from about 0.2 to about 20. The process may suitably be carried out in fixed, moving, or fluid catalyst beds. If it is desired to continuously control the extent of coke loading, moving or fluid bed configurations are preferred. With moving or fluid bed configurations, the extent of coke loading can be controlled by varying the severity and/or the frequency of continuous oxidative regeneration in a catalyst regenerator. One example of a suitable fluidized bed process for methylating toluene includes staged injection of the methylating agent at one or more locations downstream of the toluene feed location. Such a process in described in U.S. Pat. No. 6,642,426, the entire contents of which are incorporated herein by reference.

Using various of the present processes, toluene can be alkylated with methanol so as to produce para-xylene at a selectivity of at least about 75 wt % (based on total $C_8$ aromatic product) at a per-pass aromatic conversion of at least about 15 wt % and a trimethylbenzene production level less than 1 wt %. Unreacted toluene and methylating agent and a portion of the water by-product may be routed to an alkylating agent recovery zone as hereinabove described (with or without separation of methylating agent from toluene), and/or they can be recycled to the methylation reactor. The $C_8$ fraction is routed to a para-xylene separation section, which typically operates by fractional crystallization or by selective adsorption or both to recover a para-xylene product stream from the alkylation effluent and leave a para-xylene-depleted stream containing mainly $C_7$ and $C_8$ hydrocarbons.

EXAMPLES

Example 1

This simulated example illustrates the effect of performing a blowdown separation on methanol feedstock with varying levels of metal salt (here, sodium salt) contamination, based upon calculations and mass balances for methanol feedstock of 1 ppmw sodium and for methanol feedstock of 0.32 ppmw sodium, using blowdown operation resulting in 0, 3, and 7% liquid blowdown, by weight of feedstock. Sodium buildup on the aluminosilicate zeolite catalyst was calculated for long-term operations and found to increase until asymptotically approaching a maximum buildup concentration after 60 months of operation. As can be seen in Tables 1a and 1b below, exponential improvement in prevention of sodium buildup is achieved from 0 to 3% blowdown, but improvement becomes marginally lower (virtually linear) for 3 to 7% blowdown, indicating a potentially significant loss of efficiency in operating to achieve lower even concentrations of sodium.

TABLE 1a

Sodium Concentrations for 1 ppmw Sodium in Methanol Feedstock

| Blowdown % | Na in Reaction Feed (ppmw) | Na Buildup on Catalyst (ppmw) |
|---|---|---|
| 0 | 1.000 | 2041.000 |
| 3 | 0.034 | 69.390 |
| 7 | 0.015 | 30.620 |

TABLE 1b

Sodium Concentrations for 0.32 ppmw Sodium in Methanol Feedstock

| Blowdown % | Na in Reaction Feed (ppmw) | Na Buildup on Catalyst (ppmw) |
|---|---|---|
| 0 | 0.32 | 653.120 |
| 3 | 0.011 | 22.210 |
| 7 | 0.005 | 9.800 |

Example 2

Figure 6:
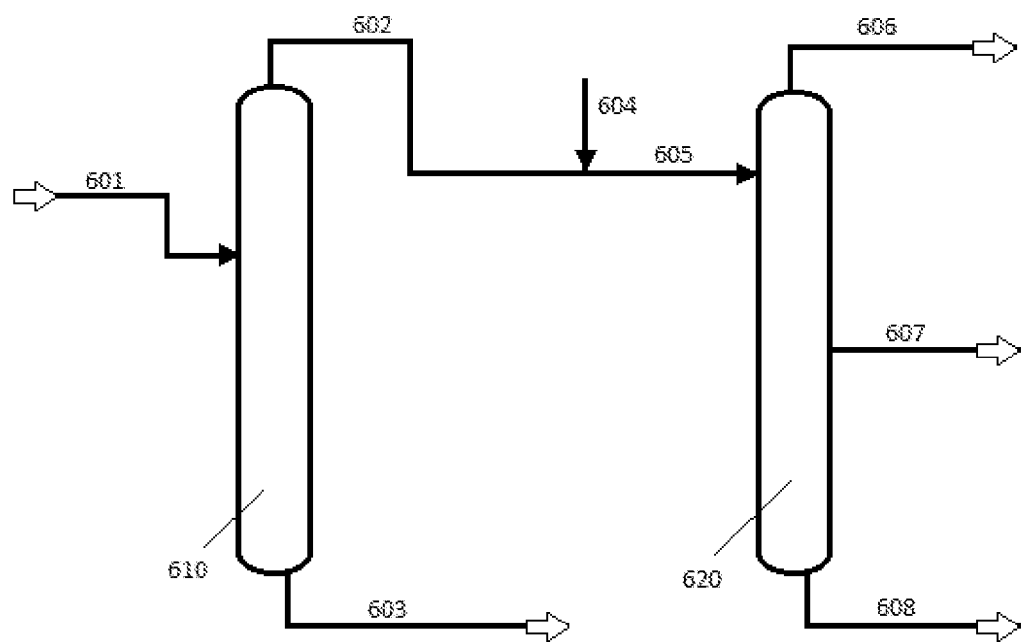
FIG. 6 is a schematic diagram illustrating a simulated example system for treating feedstock for the production of alkyl aromatics designed according to some embodiments of the invention.

This example illustrates a simulated system employing a process according to various embodiments, the system configured substantially as shown in FIG. 6. Simulations according to this example were carried out using SimSci™ PRO/II™ process simulation software, commercially available from Invensys, Inc. The system includes a liquid methanol inlet feed 601 (which may be considered as either feedstock or blowdown for purposes of this example) delivered to desalting column 610. The desalting column 610 in this example is a distillation column. The desalting column discharges methanol-rich overhead in line 602 and bottoms enriched in water (and dissolved metal salts) in line 603. The desalting column 610 as simulated included partial recycle of the bottoms via a reboiler, and partial recycle of the overhead via a condenser, which are omitted from FIG. 6 for simplicity. Overhead 602 is combined with methanol recycle stream 604 (e.g., from a reactor for methylation of toluene, not shown), forming stream 605 fed into the top of methanol stripper 620. Methanol stripper 620 discharges overhead 606 comprising water, methanol, and trace hydrocarbons in 100% vapor phase (i.e., having no entrained liquid and therefore no dissolved metal salts). Methanol stripper 620 further discharges sidestream 607 and bottoms 608 (part of which was reboiled and recycled to methanol stripper 620 as simulated, again omitted from FIG. 6 for simplicity). Table 2 illustrates the composition of each stream 601-608, showing successful operation of the simulated system in accordance with various of the embodiments described herein.

As shown in Table 2, almost no methanol is discharged from the system (i.e., in lines 603 and lines 608), while the methanol feed for delivery to alkylation reaction (line 606) includes no entrained liquid and therefore no metal salts.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for producing para-xylene, the process comprising:
   (a) separating a feedstock comprising an alkylating agent and a metal salt into at least an alkylating agent-rich vapor stream and a metal salt-enriched liquid blowdown comprising alkylating agent and metal salt, wherein the alkylating agent-rich vapor stream comprises less than 0.1 wppm metal salt;
   (b) reacting at least a portion of the alkylating agent-rich vapor stream with benzene and/or toluene in the presence of an aluminosilicate zeolite catalyst under alkylation conditions to yield para-xylene, wherein the aluminosilicate zeolite catalyst comprises a porous crystalline material having a Diffusion Parameter for 2,2 dimethylbutane of about 0.1-15 sec-1 when measured at a temperature of 120° C. and a 2,2 dimethylbutane pressure of 60 torr (8 kPa), and wherein the alkylation conditions comprise a temperature from 350 to 700° C., a pressure from 100 to 7000 kPa, and a weight hourly space velocity from 0.5 to 1000 $hr^{-1}$,
   (c) sorbing at least a portion of the metal salt from the metal salt-enriched liquid blowdown so as to form an alkylating agent-rich liquid stream and a first metal salt-rich liquid effluent;
   (d) separating the alkylating agent-rich liquid steam into an additional alkylating agent-rich vapor stream and a second metal salt-rich liquid effluent; and
   (e) flowing a sidestream produced from the separating in (d) to the reacting in (b), wherein the sidestream comprises steam.

2. The process of claim 1, further comprising:
   (f) emitting the first metal salt-rich liquid effluent and the second metal salt-rich liquid effluent together as a metal salt-rich liquid discharge; and
   (g) reacting the additional alkylating agent-rich vapor stream with one or more aromatic compounds in the presence of the aluminosilicate zeolite catalyst under alkylation conditions to yield para-xylene.

TABLE 2

Stream Compositions of Example 2

| Feed | 601 | 602 | 603 | 604 | 605 | 606 | 607 | 608 |
|---|---|---|---|---|---|---|---|---|
| Phase | Liquid | Liquid | Liquid | Liquid | Liquid | Vapor | Vapor | Mixed |
| Temp. (° C.) | 110.5 | 119.2 | 160.6 | 107.6 | 108.8 | 150.2 | 160.6 | 160.9 |
| Kg/hr | 3,287.4 | 3,252.1 | 35.3 | 57,302.3 | 6,0554.4 | 23,520.8 | 7,985.7 | 29,047.9 |
| Water* | 1.41 | 0.34 | 99.995 | 89.59 | 84.79 | 60.89 | 99.91 | 99.99 |
| Methanol* | 98.59 | 99.66 | 50 ppm | 8.63 | 13.52 | 34.80 | .23 ppm | 9.8 ppt[†] |
| Toluene* | 0 | 0 | 0 | 0.13 | 0.12 | 0.31 | 0 | 0 |
| Misc. other Hydrocarbon* | 0 | 0 | 0 | 1.66% | 1.57% | 4.00% | 877 ppm | 108 ppm |

*Compositions are in wt % unless otherwise noted
[†]ppt = parts per trillion

3. The process of claim 2, wherein the metal salt-rich liquid discharge comprises 99.9% or more by weight of the metal salt of the feedstock.

4. The process of claim 1, wherein the alkylating agent comprises methanol, dimethyl ether, or a combination thereof.

5. The process of claim 1, wherein the metal salt comprises sodium.

6. The process of claim 1, wherein the porous crystalline material comprises ZSM-5 that has undergone prior treatment with steam at a temperature of at least 950° C.

7. The process of claim 1, wherein the conditions of the (b) reacting are such that selectivity to para-xylene is at least 75%.

8. The process of claim 1, wherein the liquid blowdown comprises about 5 to about 10% by weight of the feedstock.

9. The process of claim 8, wherein the liquid blowdown comprises about 7% by weight of the feedstock.

10. The process of claim 1, wherein the sidestream comprises substantially no metal-salts and comprises less than 100 ppm of alkylating agent.

11. The process of claim 10, wherein the side stream comprises less than 1 ppm of alkylating agent.

12. The process of claim 11, further comprising:
(h) merging a stream of aromatic compounds with the side stream prior to the flowing in (e).

13. The process of claim 1, further comprising:
(i) recycling at least a portion of the second metal salt-rich liquid effluent to the sorbing in (c).

\* \* \* \* \*